US010881623B2

(12) United States Patent
Majeed et al.

(10) Patent No.: US 10,881,623 B2
(45) Date of Patent: Jan. 5, 2021

(54) COMPOSITIONS FOR THE MANAGEMENT OF HYPERGLYCEMIA AND RELATED CONDITIONS

(71) Applicants: Muhammed Majeed, Edison, NJ (US); Kalyanam Nagabhushanam, East Windsor, NJ (US); Lakshmi Mundkur, Bangalore (IN)

(72) Inventors: Muhammed Majeed, Edison, NJ (US); Kalyanam Nagabhushanam, East Windsor, NJ (US); Lakshmi Mundkur, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/232,242

(22) Filed: Dec. 26, 2018

(65) Prior Publication Data
US 2019/0192448 A1  Jun. 27, 2019

Related U.S. Application Data

(60) Provisional application No. 62/610,565, filed on Dec. 27, 2017.

(51) Int. Cl.
| | |
|---|---|
| *A61K 31/065* | (2006.01) |
| *A61K 31/05* | (2006.01) |
| *A61K 36/71* | (2006.01) |
| *A61K 47/22* | (2006.01) |
| *A61K 47/14* | (2017.01) |
| *A61K 31/191* | (2006.01) |
| *A61K 31/704* | (2006.01) |
| *B01D 11/02* | (2006.01) |
| *A61K 31/122* | (2006.01) |
| *A61K 47/12* | (2006.01) |
| *A61P 39/06* | (2006.01) |
| *A61P 3/10* | (2006.01) |
| *A61P 29/00* | (2006.01) |
| *A61K 31/19* | (2006.01) |

(52) U.S. Cl.
CPC ............ *A61K 31/05* (2013.01); *A61K 31/065* (2013.01); *A61K 31/122* (2013.01); *A61K 31/19* (2013.01); *A61K 31/191* (2013.01); *A61K 31/704* (2013.01); *A61K 36/71* (2013.01); *A61K 47/12* (2013.01); *A61K 47/14* (2013.01); *A61K 47/22* (2013.01); *A61P 3/10* (2018.01); *A61P 29/00* (2018.01); *A61P 39/06* (2018.01); *B01D 11/0203* (2013.01); *B01D 11/0288* (2013.01); *A61K 2236/00* (2013.01); *B01D 11/0211* (2013.01); *B01D 11/0292* (2013.01)

(58) Field of Classification Search
CPC .. A61K 31/065; A61K 31/122; A61K 31/704; A61K 31/19; A61P 29/00; A61P 3/10; A61P 39/06
USPC .......................................................... 514/27
See application file for complete search history.

(56) References Cited

PUBLICATIONS

Ceylan et al. (J Enzyme Inhib Med Chem, 2016; 31(6): 983-990).*
Farkhondeh et al. (Asian Pacific Journal of Tropical Medicine 2017; 10(9): 849-854).*
Fararh et al. (Research in Veterinary Science 79 (2005) 219-223).*
Ismail et al. (Journal of Applied Pharmaceutical Science vol. 5 (09), pp. 082-088, Sep. 2015).*
Sudhir et al. (IJPSR, 2016; vol. 7(8): 3185-3196).*
Kesarwani et al. (Asian Pac J Trop Biomed 2013; 3(4): 253-266).*
Benhaddou-Andalouss et al. (Pharmaceutical Biology 2008, vol. 46, Nos. 1-2, pp. 96-104).*
Sultana et al. (Journal of Pharmacognosy and Phytochemistry 2015; 4(4): 103-106).*
American Diabetes Association, https://www.diabetes.org/diabetes/medication-management/oral-medication/what-are-my-options#:~:text=Metformin%20(Glucophage)%20is%20a%20biguanide,taken%20two%20times%20a%20day.
Alkharfy et al., (2014) Pharmacokinetic plasma behaviors of intravenous and oral bioavailability of thymoquinone in a rabbit model, Eur J Drug Metab Pharmacokinet, DOI 10.1007/s13318-014-0207-8).
Amin et al., (2016) Black Cumin (*Nigella sativa*) and Its Active Constituent, Thymoquinone: An Overview on the Analgesic and Anti-inflammatory Effects, Planta Medica, 82, 8-16.

* cited by examiner

*Primary Examiner* — Shaojia A Jiang
*Assistant Examiner* — Michael C Henry (57) ABSTRACT

Disclosed is a method for therapeutic management of hyperglycemia in mammals using compositions containing thymohydroquinone. More specifically, the invention discloses compositions containing thymohydroquinone for inhibiting the activity of the enzyme α-glucosidase and increasing the cellular uptake of glucose by mammalian cells. The antioxidant, anti-inflammatory and anti-glycation effects of thymohydroquinone are also disclosed herein.

6 Claims, 6 Drawing Sheets

COMPOSITIONS FOR THE MANAGEMENT OF HYPERGLYCEMIA AND RELATED CONDITIONS

CROSS REFERENCE TO RELATED APPLICATION

This is a non-provisional US patent application claiming priority from U.S. Provisional application No. 62/610,565 filed on 27 Dec. 2017, the details of which are being incorporated herein by reference.

BACKGROUND OF THE INVENTION

Field of the Invention

The present invention relates to therapeutic management of hyperglycemia in mammals. More specifically, the present invention relates to compositions comprising thymohydroquinone and their therapeutic potential in the management of hyperglycemia and related conditions thereof.

Description of Prior Art

Hyperglycemia is a condition wherein the glucose levels in the blood remain elevated. Chronic hyperglycemia, if left untreated can cause secondary complications that lead to the development of many diseases like diabetes, obesity, hyperlipoproteinemia, hyperlipidemia, cardiovascular complications, cancer, atherosclerosis, neurodegenerative disorders, allergy, inflammation, and osteoporosis. The increased glucose levels in blood increases the production of reactive oxygen/nitrogen species and pro-inflammatory cytokines thereby causing oxidative stress and inflammation. Elevated glucose levels further increase the non-enzymatic glycosylation of proteins and other biomolecules (glycation) leading to the production Advanced glycation end products (AGEs) which are reported to be main cause for cellular aging. AGEs also exemplify the cellular inflammatory cascade leading to progressive deterioration and apoptosis.

The current drugs which are administered (e.g metformin) are effective in controlling the blood glucose levels. Continuous intake of these synthetic drugs causes many side effects which include hepatotoxicity and nephrotoxicity. Thus, a more safe and effective natural plant based molecule is warranted to manage blood glucose levels.

The treatment methods that are currently employed in the management of hyperglycemia include administering inhibitors against key enzymes that regulate carbohydrate breakdown and increasing glucose uptake. In this aspect, glucosidase inhibitors are of particular importance (Kim et al., Isolation and characterization of α-glucosidase inhibitor from the fungus *Ganoderma lucidum*. Journal of Microbiology, 2013; 42:223-227). α-glucosidase, is essential for the degradation of glycogen to glucose. It acts on complex carbohydrate molecules to yield monosaccharide units which are readily absorbed in the blood stream. Inhibiting α-glucosidase results in the reduction of glucose release into the blood stream thereby decreasing the hyperglycemic condition.

There are many plant based inhibitory molecules for α-glucosidase which are discussed in the following prior arts:
1. Thilagam et al., α-Glucosidase and α-Amylase Inhibitory Activity of *Senna surattensis*, Journal of Acupuncture and Meridian Studies, 2013; 6(1):24-30
2. Poongunran et al., α-Glucosidase and α-Amylase Inhibitory Activities of Nine Sri Lankan Antidiabetic Plants, British Journal of Pharmaceutical Research, 2015; 7(5): 365-374.
3. Kim et al., Isolation and characterization of α-glucosidase inhibitor from the fungus *Ganoderma lucidum*. Journal of Microbiology, 2013; 42:223-227.

However, a plant based molecule that effectively inhibits α-glucosidase and increases glucose uptake is required for effective management of hyperglycemia and related conditions.

*Nigella sativa* is well known for its many therapeutic properties in the Ayruvedic, Siddha and Unani systems of medicine. The plant is reported to contain many active molecules like thymoquinone, thymohydroquinone, dithymoquinone, p-cymene, carvacrol, 4-terpineol, t-anethol, sesquiterpene longifolene, α-pinene, thymol, α hederin and hederagenin (Ahmad et al., A review on therapeutic potential of *Nigella sativa*: A miracle herb, Asian Pac J Trop Biomed. 2013; 3(5): 337-352), which are responsible for the beneficial effects of the plant. Some of the therapeutic effects of *Nigella sativa* are listed in the following prior art documents:
1. Alimohammadi et al., Protective and antidiabetic effects of extract from *Nigella sativa* on blood glucose concentrations against streptozotocin (STZ)—induced diabetic in rats: an experimental study with histopathological evaluation, Diagn Pathol. 2013; 8: 137.
2. Sultana et al., Nigella sativa: Monograph, Journal of Pharmacognosy and Phytochemistry 2015; 4(4): 103-106.
3. Randinva and Alghamdi, Anticancer activity of *Nigella sativa* (black seed)—a review, Am J Chin Med. 2011; 39(6):1075-91.
4. Mahmood et al., *Nigella sativa* an Antiglycating Agent for Human Serum Albumin, International Journal of Scientific research, 2013; 2(4):25-27
5. Sobhi et al., Effect of lipid extracts of *Nigella sativa* L. seeds on the liver ATP reduction and alpha-glucosidase inhibition, Pak J Pharm Sci., 2016; 29(1):111-117.
6. Awasthi S, Understanding the mechanism of antidiabetic activity and efficacy of functional foods against advanced glycation end products: *Nigella saliva* and *Moringa oleifera*, Planta Med, 2013; 79-PN8

Most of the reported biological effects of *Nigella sativa* are either for the whole extract or specifically for thymoquinone. Reports on the biological effects of the thymohydroquinone, especially with respect to the management of hyperglycemia are not available. Although thymohydroquinone is the reduced form of thymoquinone it is different both structurally and functionally. The present invention thus discloses a novel and non-obvious compositions enriched with thymohydroquinone for the management of hyperglycemia and related disorders.

It is the principle object of the invention to disclose a method for the inhibiting the activity of α-Glucosidase using a composition comprising thymohydroquinone.

It is another object of the invention to disclose a method of increase the uptake of glucose by mammalian cells by administering a composition comprising thymohydroquinone.

It is yet another object of the invention to disclose a method for therapeutic management of hyperglycemia and related disorders in mammals using a composition comprising thymohydroquinone.

The present invention solves the above mentioned objectives and provides further related advantages.

SUMMARY OF THE INVENTION

The present invention discloses novel compositions comprising thymohydroquinone. Specifically, the invention discloses compositions containing thymohydroquinone for inhibiting the activity of the enzyme α-Glucosidase. The invention also discloses the use of compositions containing thymohydroquinone for increasing the cellular uptake of glucose by mammalian cells. More specifically the invention discloses a method for therapeutic management of hyperglycemia in mammals using compositions containing thymohydroquinone. The anti-oxidant, anti-inflammatory and anti-glycation effects of thymohydroquinone are also disclosed herein.

Other features and advantages of the present invention will become apparent from the following more detailed description, taken in conjunction with the accompanying drawings, which illustrate, by way of example, the principle of the invention.

DESCRIPTION OF THE MOST PREFERRED EMBODIMENTS

In a most preferred embodiment, the invention discloses a method of inhibiting glucosidase enzyme, said method comprising steps of:
i) Bringing into contact glucosidase enzyme with a paranitrophenyl-α-d-glucopyranoside substrate;
ii) Incubating with an effective doses of thymohydroquinone or a composition comprising thymohydroquinone under optimal conditions;
iii) Reading the change in absorbance using spectrophotometric and fluorimetric methods
iv) Comparing the absorbance with a control blank and determining the percentage enzyme inhibition ($IC_{50}$) by thymohydroquinone or a composition comprising thymohydroquinone using the formula:

% Inhibition=[(absorbance of control−absorbance of inhibitor)/absorbance of control]×100

In a related embodiment, the composition comprises of about 0.1%-5% w/w thymoquinone, about 0.01%-10% w/w thymohydroquinone, about 20%-95% w/w fatty acids, about 0.001%-3% w/w α-hederin or hederagenin, 0.1%-4.0% w/w stabilizing agent and 0.2%-2% w/w bioavailability enhancer. In another related embodiment, the stabilizing agent is selected from the group comprising rosmarinic acid, butylated hydroxyanisole, butylated hydroxytoluene, sodium metabisulfite, propyl gallate, cysteine, ascorbic acid and tocopherols. In yet another related embodiment the bioavailability enhancer is selected from the group comprising piperine, quercetin, garlic extract, ginger extract, and naringin.

In another most preferred embodiment, the invention discloses a method of increasing glucose uptake by mammalian cells, said method comprising steps of bringing into contact mammalian cells with effective dose of thymohydroquinone or a composition comprising thymohydroquinone, to increase glucose uptake by the cells. In a related embodiment, the composition comprises of about 0.1%-5% w/w thymoquinone, about 0.01%-10% w/w thymohydroquinone, about 20%-95% w/w fatty acids, about 0.001%-3% w/w α-hederin or hederagenin, 0.1%-4.0% w/w stabilizing agent and 0.2%-2% w/w bioavailability enhancer. In another related embodiment, the stabilizing agent is selected from the group comprising rosmarinic acid, butylated hydroxyanisole, butylated hydroxytoluene, sodium metabisulfite, propyl gallate, cysteine, ascorbic acid and tocopherols. In yet another related embodiment the bioavailability enhancer is selected from the group comprising piperine, quercetin, garlic extract, ginger extract, and naringin. In another related embodiment, the mammalian cells are human cells.

In another preferred embodiment, the invention discloses a method for the therapeutic management of hyperglycemia and related conditions in mammals, said method comprising steps of administering effective dose of thymohydroquinone or a composition comprising thymohydroquinone, to bring about a reduction in the levels of glucose in the blood. In a related embodiment, the management of hyperglycemia and related conditions is brought about by decreasing absorption of glucose by inhibiting glucosidase enzyme, increasing cellular uptake of glucose, reducing free radicals, reducing inflammation and decreasing glycation. In another related embodiment, the hyperglycemia related conditions are present in disease states selected from the group comprising diabetes, obesity, hyperlipoproteinimia, hyperlipidemia, cardiovascular complications, cancer, atherosclerosis, neurodegenerative diseases, allergy, inflammation, and osteoporosis. In a related embodiment, the composition comprises of about 0.1%-5% w/w thymoquinone, about 0.01%-10% w/w thymohydroquinone, about 20%-95% w/w fatty acids, about 0.001%-3% α-hederin or hederagenin, 0.1%-4.0% w/w stabilizing agent and 0.2%-2% w/w bioavailability enhancer. In another related embodiment, the stabilizing agent is selected from the group comprising rosmarinic acid, butylated hydroxyanisole, butylated hydroxytoluene, sodium metabisulfite, propyl gallate, cysteine, ascorbic acid and tocopherols. In yet another related embodiment the bioavailability enhancer is selected from the group of piperine, quercetin, garlic extract, ginger extract, and naringin. In another related embodiment, the mammalian cells are human cells. In another related embodiment, the composition is formulated with pharmaceutically/inutraceutically acceptable excipients, adjuvants, diluents or carriers and administered orally in the form of tablets, capsules, soft gels, syrups, gummies, powders, suspensions, emulsions, chewables, candies or eatables.

The aforesaid most preferred embodiments incorporating the technical features and technical effects of instant invention, are explained through illustrative examples herein under.

EXAMPLE 1: INHIBITION OF GLUCOSIDASE

For glucosidase inhibition, α-glucosidase (Code G5003; Sigma-Aldrich, St. Louis, Mo., USA) was dissolved in 67 mM potassium phosphate buffer, pH 6.8, containing 8 containing 0.2% Bovine Serum Albumin (Sigma-Aldrich) & 0.02% sodium azide (Sigma-Aldrich) which was used as enzyme source. Paranitrophenyl-α-d-glucopyranoside (Sigma-Aldrich) was used as substrate. Thymoquinone, thymohydroquinone and composition containing thymohydroquinone were weighed prepared at concentration of 63, 125, 250 and 500 µg/ml and were made up with equal volumes of distilled water. 50 µl of said composition was incubated for 5 min with 50 µl enzyme source (0.15 U/ml). After incubation, 50 µl of substrate (1.25 mM) was added and further incubated for 20 min at room temperature. Presubstrate and post-substrate addition, absorbance was measured at 405 nm on a microplate reader (BMG FLUOstar OPTIMA Microplate Reader). The increase in absorbance on substrate addition was obtained. Each test was performed three times and the mean absorption was used to calculate percentage α-glucosidase inhibition. Acarbose was used as positive control with various concentrations. The inhibitory activities of varying concentrations of said composition were expressed as 100 minus the absorbance difference (%) of the said composition relative to the absorbance change of the negative control (i.e., water used as the test solution). The measurements were performed in triplicate, and the $IC_{50}$ value (i.e., the concentration of said composition that results in 50% inhibition of maximal activity) was determined.

Figure 1A:
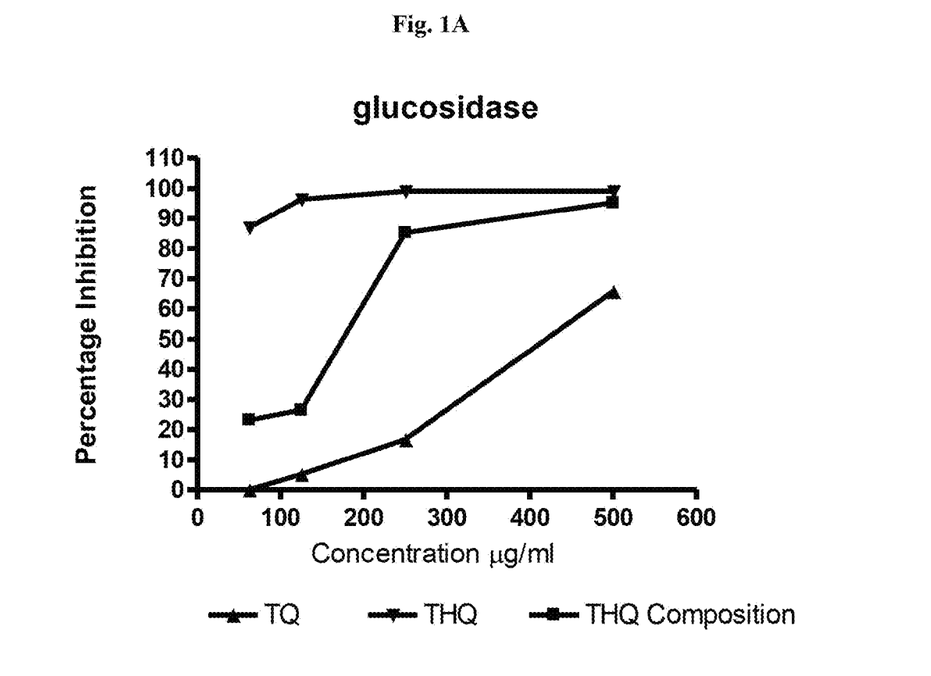
FIG. 1A and FIG. 1B shows the graphical representation α-glucosidase inhibitory activity of thymoquinone (TQ), thymohydroquinone (THQ) and thymohydroquinone composition.
Figure 1B:
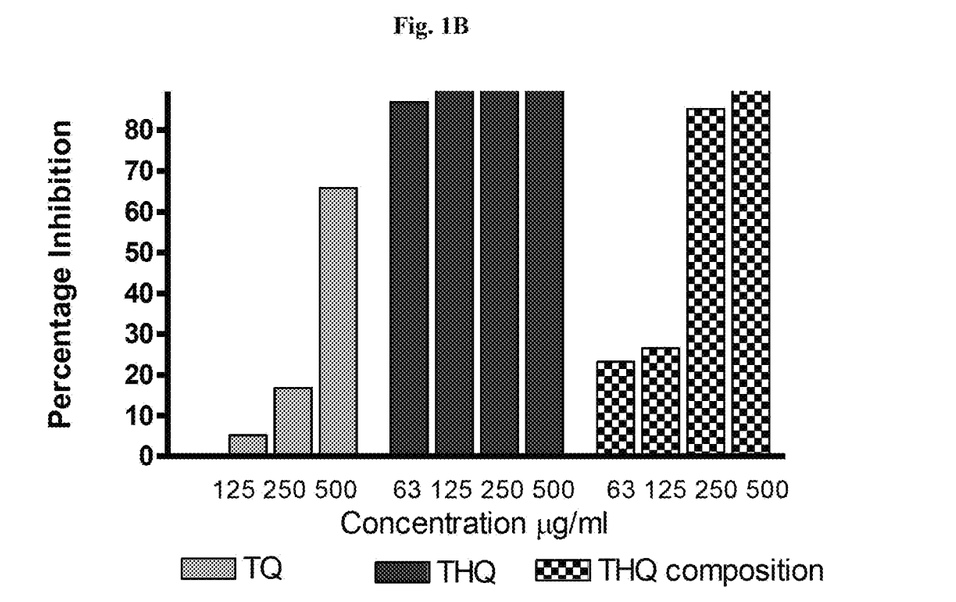

Thymohydroquinone ($IC_{50}$ 71.9 µg/ml) and the composition comprising thymohydroquinone ($IC_{50}$ 150.9 µg/ml) exhibited effective inhibition of a glucosidase when compared to thymoquinone ($IC_{50}$ 407.6 µg/ml) (FIG. 1A and FIG. 1B).

EXAMPLE 2: INCREASE IN GLUCOSE UPTAKE

The skeletal muscle cell line C2C12 myoblasts (procured from ATCC) were maintained in DMEM supplemented with 10% Fetal Bovine Serum at 37° C. with 5% $CO_2$. Twenty thousand cells per well were seeded in a 24 well plate. When the cells reached 80-90% confluence, differentiation was induced by replacing the growth medium with DMEM containing 1% horse serum. Experiments were performed in completely differentiated C2C12 myotubes after 4-5 days in differentiation medium. Cells were then treated with 0.5% BSA in low glucose media for 16 hours and washed with cold Krebs-Ringer phosphate buffer without glucose. Cells were then treated with different non cytotoxic concentrations of samples in low glucose DMEM media with or without insulin at a concentration of 0.1 µM for 30 minutes at 37° C. Cells were then washed with cold PBS and stained with 5 µM of a fluorescent D-glucose analog 2-[N-(7-nitrobenz-2-oxa-1,3-diazol-4-yl) amino]-2-deoxy-D-glucose (2-NBDG) for 15 minutes in dark followed by flow cytometric detection of fluorescence produced by the cells.

Figure 2A:
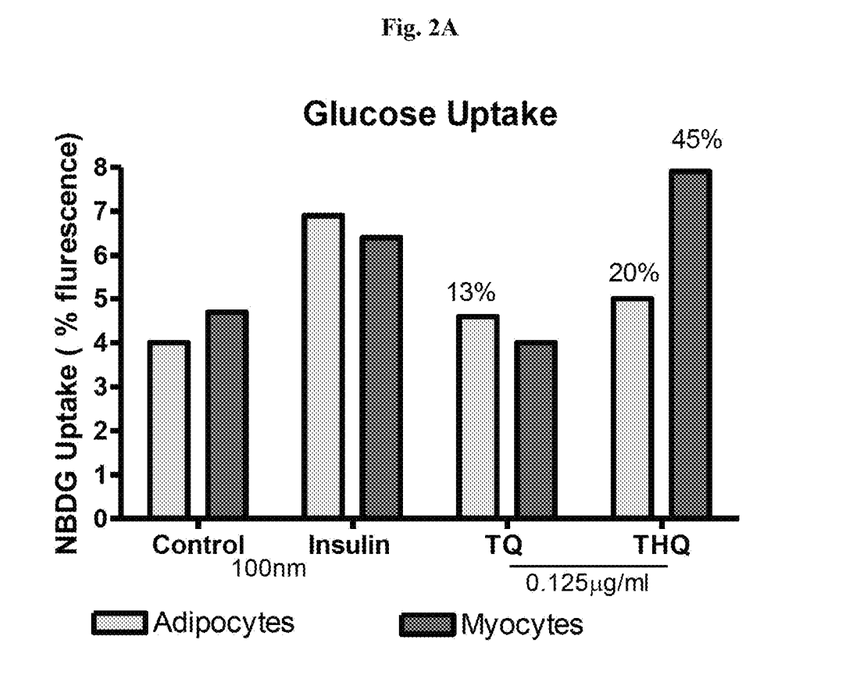
FIG. 2A and FIG. 2B are graphical representations showing the percentage glucose uptake by adipocytes and myocytes treated with thymoquinone (TQ), thymohydroquinone (THQ) and thymohydroquinone composition.
Figure 2B:
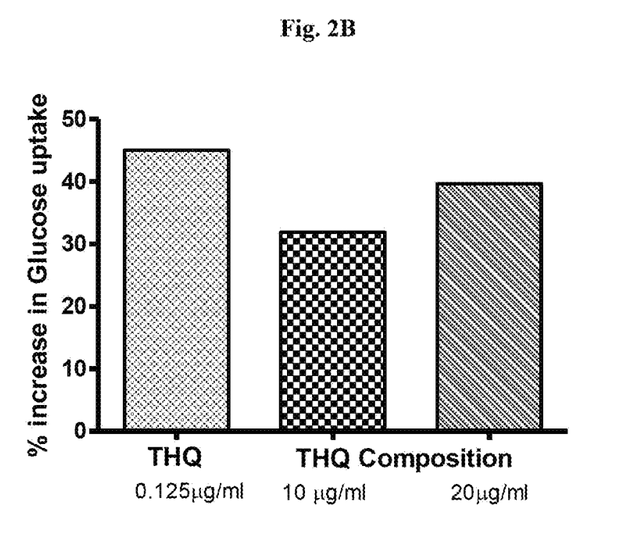
Figure 3A:
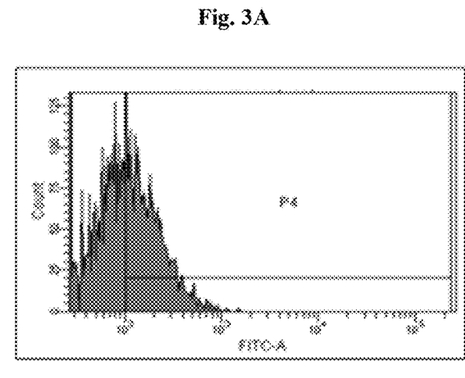
FIGS. 3A, 3B, 3C, 3D and 3E show the representative histograms of glucose uptake by mammalian cells treated with Insulin (3A), thymoquinone (TQ) (3B), thymohydroquinone (THQ) (3C), and thymohydroquinone composition (3D), Un-treated cell serve as control group (3E).
Figure 3B:
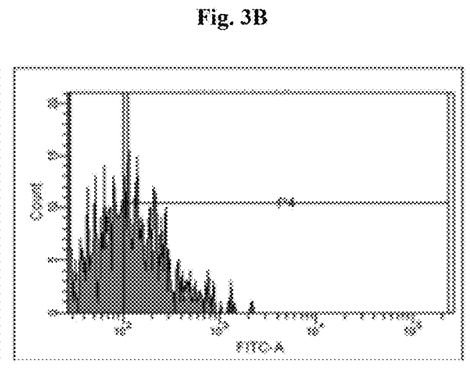
Figure 3C:
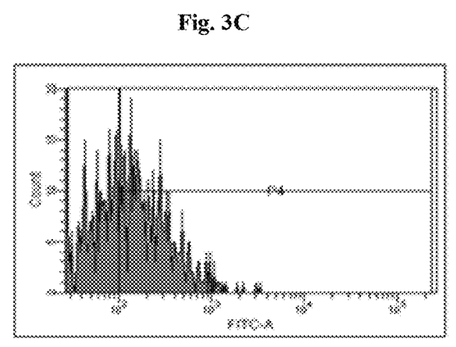
Figure 3D:
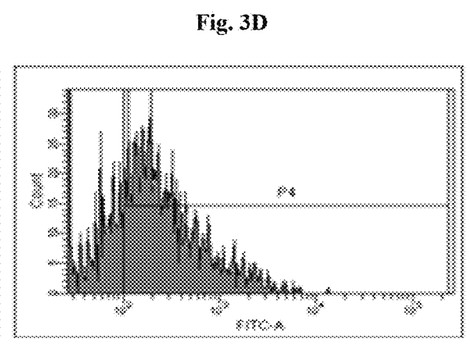
Figure 3E:
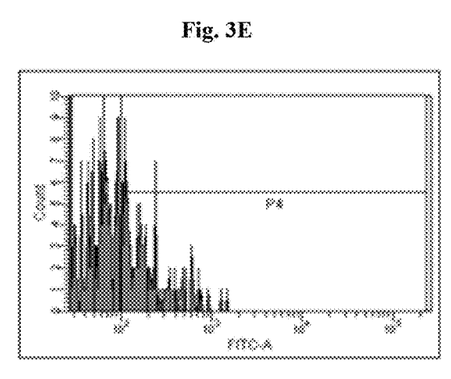

Thymohydroquinone and the composition comprising thymohydroquinone showed enhanced glucose uptake in Adipocytes and Muscle cells when compared to thymoquinone (FIG. 2A and FIG. 2B).

EXAMPLE 3: ANTI-OXIDANT ACTIVITY OF THYMOHYDROQUINONE

The antioxidant property of thymohydroquinone was assessed by DPPH scavenging activity.

Chronic increase of sugar levels in the blood leads to the formation of reactive oxygen species. Reactive oxygen species (ROS) including superoxide, hydroxyl, peroxyl, and alkoxy radicals are scavenged by the cellular anti oxidants and remain in equilibrium. These ROS induced damage causes skin irritation, inflammation, ageing, cancer and many other diseases. α,α-diphenyl-β-picrylhydrazyl (DPPH) free radical scavenging method is one of the first approach for evaluating the antioxidant potential of a compound.

Procedure

DPPH is a stable free radical in a methanolic solution with an absorbance at 520 nm. If the free radicals are scavenged by an anti oxidant molecule, the resulting solution appears yellow. The hydrogen atoms or electrons donation ability of the extracellular metabolite was measured by the bleaching of purple coloured DPPH methanol solution.

Thymoquinone, Thymohydroquinone and the composition comprising thymohydroquinone were prepared in varying concentrations. For the DPPH radical scavenging assay, 20 µL of test material was mixed with 180 µL of DPPH in methanol in a 96 well plate following the method as described earlier (Clarke et al., 2013). The plate was kept in the dark for 15 min, after which the absorbance of the solution was measured at 540 nm using a microplate reader (TECAN Ltd, Männedorf, Switzerland). Blanks (DMSO, methanol) and standard (Trolox solution in DMSO) were recorded simultaneously. The extracts were screened with variable concentrations to establish the inhibition concentration ($IC_{50}$, the concentration reducing DPPH absorbance by 50%).

The free radical scavenging activity was calculated as follows, $$\% \text{ scavenging activity} = \frac{(B-C)-(S-C)}{(B-C)} \times 100$$

Figure 4A:
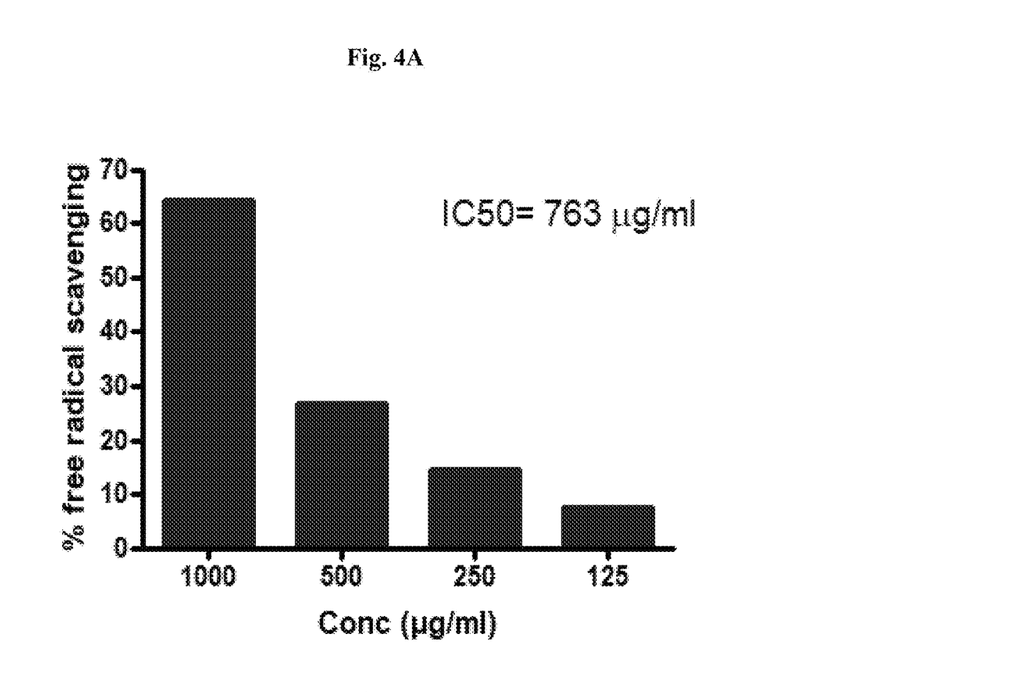
FIGS. 4A, 4B and 4C show the graphical representation of DPPH scavenging activity of thymoquinone (TQ) (4A), thymohydroquinone (THQ) (4B), and thymohydroquinone composition (4C).
Figure 4B:
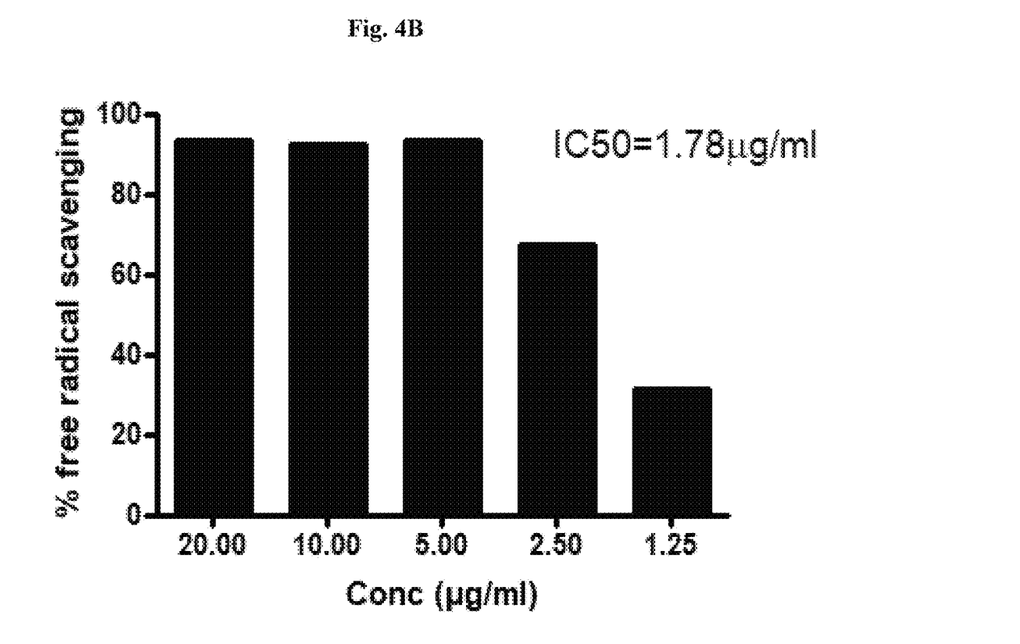
Figure 4C:
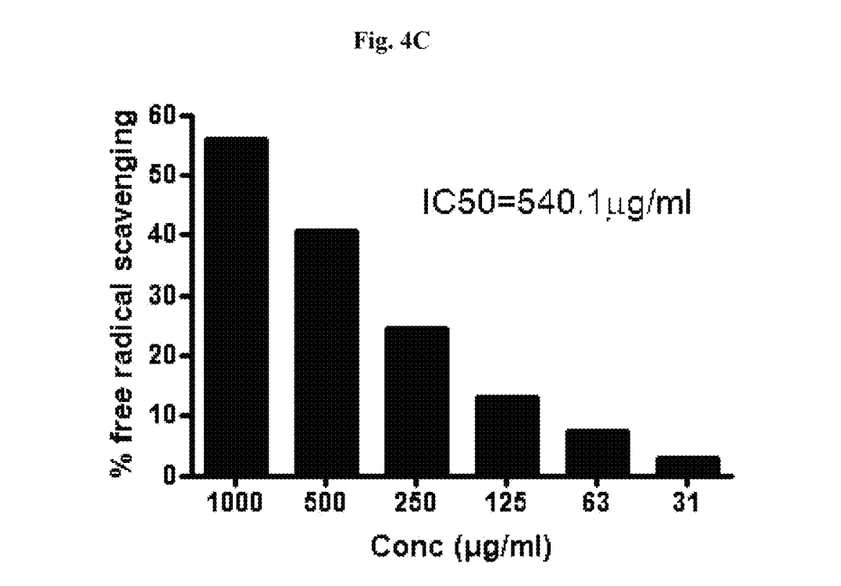

Where,
B=Absorbance of reference solution (OD of DPPH)
C=Absorbance of reference solution, blank (OD of Methanol only)
S=Absorbance of test solution
C=Absorbance of test solution blank Thymohydroquinone is a potent anti oxidant with an $IC_{50}$ of 1.78 µg/ml (FIG. 4B). The composition comprising thymohydroquinone also exhibited excellent antioxidant potential with an $IC_{50}$ of 540.1 µg/ml (FIG. 4C), which is much effective that thymoquinone (FIG. 4A).

EXAMPLE 4: ANTI-INFLAMMATORY ACTIVITY OF THYMOHYDROQUINONE

Chronic hyperglycemia increases cellular inflammation by increasing the production of pro-inflammatory cytokines like TNT-α. Thymoquinone, thymohydroquinone and a composition comprising thymohydroquinone were tested for their anti-inflammatory activity by assessing their TNF-α inhibitory activity.

Cells: THP1-human monocytes purchased from American Type Culture Collection (ATCC, Manassas, Va.) and maintained as a monolayer culture in Rosewell park memorial institute Medium (RMPI Life technologies, CA, USA.) supplemented with 10% (v/v) heat-inactivated foetal bovine serum (FBS; GIBCO/Invitrogen, Carlsbad, Calif.), 100 units/mL penicillin and 100 µg/mL streptomycin (Life technologies) at 37° C. in a humidified 5% CO2 incubator.

Reagents and buffers: Lipopolysaccharide (LPS, Sigma chemicals, USA), Phosphate buffered saline, RPMI, FBS ELISA kit: Human TNF ELISA kit, Krishgen Biosciences, USA Procedure Anti inflammatory activity was examined using human monocyte/macrophage cell line THP-Monocytes respond to lipopolysaccharides (LPS) by secreting proinflammatory cytokines. Tumour necrosis factor (TNF-α) is one of the principle cytokine which triggers a cascade of inflammatory reactions. The concentration of TNF-α was measured using an Enzyme linked Immunosorbent assay (ELISA). Reduction in TNF-α concentration indicates an anti inflammatory activity of the compound.

1×105 THP-1 cells were stimulated with 100 ng with lipopolysacharide (LPS, 0.1 µg/mL) to induce TNF-α secretion. Cells were pre treated with different concentrations of test materials (Thymoquinone, thymohydroquinone and a composition comprising thymohydroquinone) before LPS treatment. The cell supernatants were collected 24 hour after treatment and secreted TNF-α as estimated by cytokine ELISA as described by the manufacturer. Unstimulated cells were used as negative control. The limit of detection was <1 pg/mL.

Results

The results indicated the thymohydroquinone inhibited TNF-α (Table 1), indicating significant anti inflammatory activity without affecting the cell viability.

TABLE 1

Anti-inflammatory activity of thymohydroquinone

|  | Concentration (µg/mL) | % Inhibition |
|---|---|---|
| Thymoquinone | 0.13 | 35 |
|  | 0.06 | 31 |
|  | 0.03 | 22 |
| Thymohydroquinone | 0.13 | 11.9 |
|  | 0.06 | 4.5 |
|  | 0.03 | 2.5 |
| Thymohydroquinone composition | 25 | 26.2 |
|  | 12.5 | 19.8 |
|  | 6.25 | 14.9 |

EXAMPLE 5: ANTI-GLYCATION ACTIVITY OF THYMOHYDROQUINONE

Advanced glycation end products (AGEs) are generated by the non enzymatic adduct formation between amino groups of proteins (predominantly lysine and arginine) and carbonyl groups of reducing sugar, also known as Maillard reaction. In the early stages, reducing sugars react with free amino groups to form an unstable aldimine compound which undergoes molecular rearrangement to form a stable early glycation product known as Amadori product. In the later stages, glycation process through oxidation, dehydration and cyclization reactions forms the advanced glycation end products also known as AGE. Various structures of AGEs such as Nε—(carboxymethyl)-lysine (CML), pyrraline, pentosidine, are known to be associated with degenerative disorders, including aging, diabetes, atherosclerosis Alzheimer's disease, and renal failure Pentosidines are known to accumulate in diabetes patients and Vesperlysines are found in cataractogenesis and diabetic retinopathy. Agents that can prevent glycation can effectively used to counter the secondary complications associated with hyperglycemia. Thymoquinone and thymohydroquinone were tested for their anti-glycation effects.

AGEs can be fluorescent as well as non fluorescent in nature. Typically the vesperlysine type of AGE have an excitation at 370-nm and emission at 440 nm, while pentosidine like AGE have an excitation at 335 nm and emission at 385 nm. The principle is based on the fact that ribose sugar and bovine serum albumin are mixed in specific ratio and incubated for 24 hours. Vesperlysine like AGE formed by the reaction was e estimated by the increase in fluorescence detected, at Ex/Em at 390/460 nm and pentosidines were detected at Ex/Em at 320/405 nm Materials Ribose, Bovine Serum Albumin, 96 Well Black Microtitre Plates Ribose—BSA method: 10 µl of various concentrations of samples were added to 40 µl of BSA (bovine serum albumin, 25 mg/ml stock) and 50 µl of D-Ribose (150 mg/ml stock) was added per well of black 96-well microplate and incubated for 24 h at 37° C. BSA was taken as the control. The AGEs (advanced glycation end product) formed were detected by the fluorescence at Ex/Em at 390/460 nm for vesperlysine and Ex/Em at 320/405 nm for pentosidine AGE.

Results

The inhibition of the AGEs vesperlysine and Pentosidine by thymoquinone and thymohydroquinone is tabulated in table 2.

TABLE 2

Percentage inhibition of AGEs by thymohydroquinone

|  | % inhibition of vesperlysine Ex/Em at 390/460 nm | | % Inhibition of pentosidine Ex/Em at 320/405 nm | |
|---|---|---|---|---|
| Concentration (µg/mL) | TQ | THQ | TQ | THQ |
| 250 | 56.69 | 60.42 | 61.80 | 89.31 |
| 125 | 44.54 | 52.28 | 44.57 | 68.33 |
| 62.5 | 40.81 | 43.83 | 0.06 | 49.55 |
| 31.25 | 38.55 | 34.06 | 23.59 | 28.73 |
| 15.63 | 0 | 23.03 | 0 | 5.39 |
| IC$_{50}$ | 157.80 | 108.30 | 142.70 | 65.89 |

The results indicated that thymohydroquinone is biologically more potent molecule and exhibits enhanced biological activity when compared to thymoquinone.

The biological effects of compositions with increasing percentage of thymohydroquinone was also evaluated. Table 3 provides the list the compositions with increase in thymohydroquinone content.

TABLE 3

Compositions containing thymohydroquinone

| Composition | % TQ | % THQ |
|---|---|---|
| 1 | 0.643 | 0.029 |
| 2 | 0.620 | 0.093 |
| 3 | 0.558 | 0.120 |
| 4 | 0.450 | 0.250 |

Figure 5:
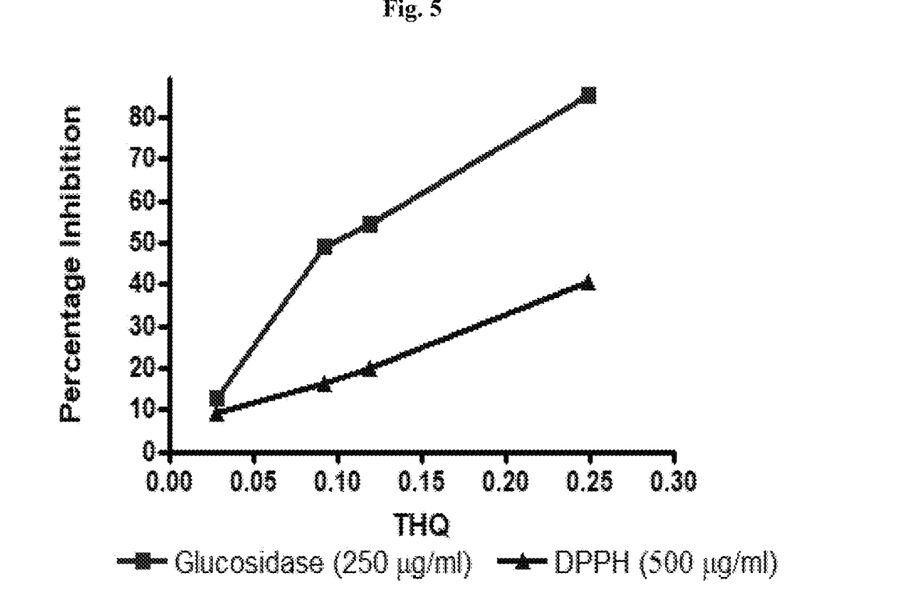
FIG. 5 shows the graphical representation of DPPH scavenging activity and glucosidase inhibition activity compositions with increasing percentages of thymohydroquinone. Increase in thymohydroquinone content directly correlated with increase in biological activity.
Figure 6:
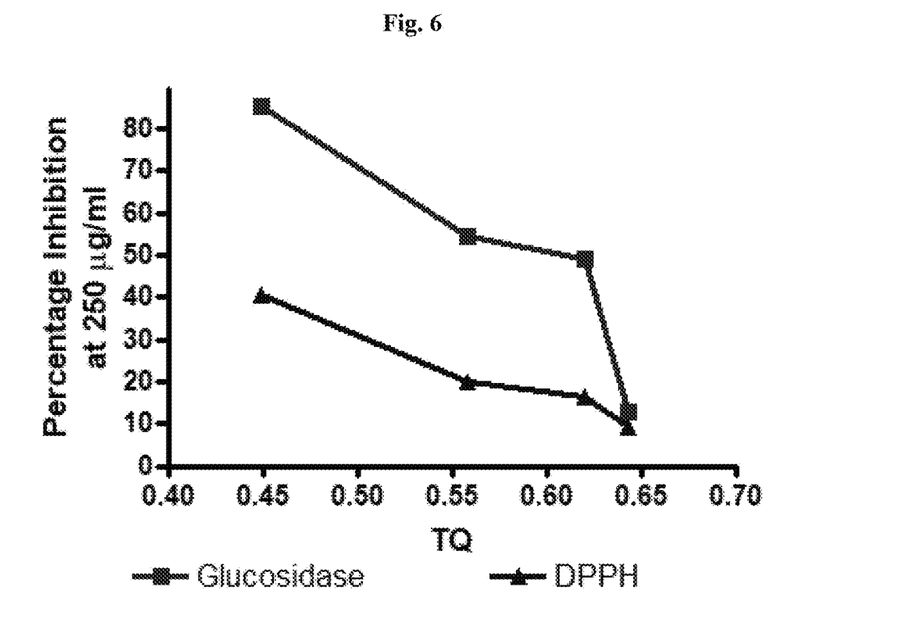
FIG. 6 shows the graphical representation of DPPH scavenging activity and glucosidase inhibition activity compositions with increasing percentages of thymoquinone. Increase in thymoquinone content inversely correlated with increase in biological activity.

Increase in thymohydroquinone content in the compositions correlated with higher DPPH scavenging and glucosidase inhibition (FIG. 5) when compared to thymoquinone, which did not show correlation with biological activity (FIG. 6). Thus, thymohydroquinone can be effectively incorporated into formulations for the effective management of various diseases and disorders including, but not limited to, hyperglycemia, diabetes, obesity, hyperlipoproteiniemia, hyperlipidemia, cardiovascular complications, cancer, atherosclerosis, neurodegenerative diseases, allergy, inflammation, and osteoporosis.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention and is to be interpreted only in conjunction with the appended claims.

We claim:

1. A method of inhibiting glucosidase enzyme, said method comprising step of bringing into contact glucosidase enzyme with an effective dose of thymohydroquinone or a composition comprising thymohydroquinone standardized to contain about 0.1%-5% w/w thymoquinone, about 0.01%-10% w/w thymohydroquinone, about 20%-95% w/w fatty acids, about 0.001%-3% w/w a-hederin or hederagenin, 0.1%-4.0% w/w rosmarinic acid and 0.2%-2% w/w piperine, the bring about the effect of glucosidase enzyme inhibition.

2. A method of increasing glucose uptake by mammalian cells, said method comprising steps of bringing into contact mammalian cells with effective dose of thymohydroquinone or a composition comprising thymohydroquinone, standardized to contain about 0.1%-5% w/w thymoquinone, about 0.01%-10% w/w thymohydroquinone, about 20%-95% w/w fatty acids, about 0.001%-3% w/w a-hederin or hederagenin, 0.1%-4.0% w/w rosmarinic acid and 0.2%-2% w/w piperine, to increase glucose uptake by the cells.

3. A method for the therapeutic management of hyperglycemia and related conditions in mammals, said method comprising steps of administering effective dose of thymohydroquinone or a composition comprising thymohydroquinone, standardized to contain about 0.1%-5% w/w thymoquinone, about 0.01%-10% w/w thymohydroquinone, about 20%-95% w/w fatty acids, about 0.001%-3% w/w a-hederin or hederagenin, 0.1%-4.0% w/w rosmarinic acid and 0.2%-2% w/w piperine to bring about a reduction in the levels of glucose in the blood.

4. The method as in claim 3, wherein the management of hyperglycemia and related conditions is brought about by decreasing absorption of glucose by inhibiting glucosidase enzyme, increasing cellular uptake of glucose, reducing free radicals, reducing inflammation and decreasing glycation.

5. The method as in claim 3, wherein the hyperglycemia related conditions are present in disease states selected from the group comprising diabetes, obesity, hyperlipoproteiniemia, hyperlipidemia, cardiovascular complications, cancer, atherosclerosis, neurodegenerative diseases, allergy, inflammation, and osteoporosis.

6. The method as in claim 3, wherein the mammal is human.

* * * * *